(12) United States Patent
McHale et al.

(10) Patent No.: US 7,972,350 B2
(45) Date of Patent: Jul. 5, 2011

(54) CATHETER TIP

(75) Inventors: Thomas McHale, Co. Galway (IE); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 639 days.

(21) Appl. No.: 10/767,675

(22) Filed: Jan. 29, 2004

(65) Prior Publication Data
US 2005/0171591 A1 Aug. 4, 2005

(51) Int. Cl.
*A61M 25/10* (2006.01)
(52) U.S. Cl. ...................................................... 606/194
(58) Field of Classification Search .................. 623/1.11;
604/509, 96.01, 264, 523, 533, 534; 606/194,
606/200, 108; 600/128, 129, 139, 141, 144
See application file for complete search history.

(56) References Cited

U.S. PATENT DOCUMENTS

| | | | | |
|---|---|---|---|---|
| 3,832,253 A | | 8/1974 | Palma at al. .................... 156/86 |
| 3,865,666 A | | 2/1975 | Shoney .......................... 156/245 |
| 3,884,242 A | | 5/1975 | Bazell et al. ................... 128/351 |
| 3,959,429 A | | 5/1976 | Benning ........................ 264/155 |
| 4,157,094 A | | 6/1979 | Patel ........................ 128/349 B |
| 4,210,478 A | | 7/1980 | Shoney .......................... 156/242 |
| 4,276,874 A | * | 7/1981 | Wolvek et al. ................... 600/18 |
| 4,284,459 A | | 8/1981 | Patel et al. ..................... 156/245 |
| 4,531,943 A | | 7/1985 | Van Tassel et al. ........... 604/280 |
| 4,597,755 A | * | 7/1986 | Samson et al. ........... 604/103.09 |
| 4,665,925 A | * | 5/1987 | Millar ............................ 600/585 |
| 4,739,769 A | * | 4/1988 | Matthews et al. ............. 600/486 |
| 4,842,590 A | | 6/1989 | Tanabe et al. .................. 604/282 |
| 5,250,069 A | * | 10/1993 | Nobuyoshi et al. ........... 606/192 |
| 5,254,091 A | * | 10/1993 | Aliahmad et al. ........ 604/103.06 |
| 5,318,032 A | | 6/1994 | Lonsbury et al. ............. 128/658 |
| 5,509,910 A | | 4/1996 | Lunn ............................. 604/282 |
| 5,514,236 A | | 5/1996 | Avellanet et al. ............. 156/154 |
| 5,549,552 A | | 8/1996 | Peters et al. |
| 5,622,665 A | | 4/1997 | Wang ............................ 264/150 |
| 5,645,528 A | | 7/1997 | Thome ........................... 604/96 |
| 5,653,691 A | | 8/1997 | Rupp et al. ...................... 604/96 |
| 5,728,063 A | | 3/1998 | Preissman et al. |
| 5,728,065 A | * | 3/1998 | Follmer et al. ............. 604/96.01 |
| 5,762,637 A | | 6/1998 | Berg et al. ..................... 604/264 |
| 5,766,203 A | * | 6/1998 | Imran et al. .................. 623/1.11 |
| 5,788,707 A | | 8/1998 | Del Toro et al. .............. 606/108 |

(Continued)

FOREIGN PATENT DOCUMENTS
EP 0611582 1/1994
(Continued)

OTHER PUBLICATIONS

English translation of EP Opponent's Brief.

*Primary Examiner* — Ryan J Severson
(74) *Attorney, Agent, or Firm* — Vidas, Arrett & Steinkraus, P.A.

(57) ABSTRACT

A catheter tip may be coupled to a catheter shaft. The catheter tip may include markers, such as radiopaque markers and MRI markers, securement hubs, recessed portions, a radiused tip, and varying axial flexibility. The catheter tip may be a molded tip, and the markers may be insert molded. Recessed portions and raised securement hubs may be formed during the molding process. The raised hubs may be integrally formed and made from the same material as the catheter tip.

29 Claims, 13 Drawing Sheets

U.S. PATENT DOCUMENTS

| | | | | |
|---|---|---|---|---|
| 5,830,401 | A | 11/1998 | Prichard et al. | 264/262 |
| 5,906,606 | A * | 5/1999 | Chee et al. | 604/527 |
| 5,921,958 | A * | 7/1999 | Ressemann et al. | 604/96.01 |
| 5,944,726 | A | 8/1999 | Blaeser et al. | 606/108 |
| 5,951,569 | A | 9/1999 | Tuckey et al. | 606/108 |
| 5,951,585 | A * | 9/1999 | Cathcart et al. | 606/198 |
| 5,968,012 | A | 10/1999 | Ren et al. | 604/96 |
| 6,007,543 | A | 12/1999 | Ellis et al. | 606/108 |
| 6,048,485 | A | 4/2000 | Field et al. | 264/322 |
| 6,074,374 | A * | 6/2000 | Fulton | 604/249 |
| 6,113,579 | A | 9/2000 | Eidenschink et al. | 604/264 |
| 6,149,996 | A | 11/2000 | Helgerson et al. | 428/36.9 |
| 6,162,229 | A | 12/2000 | Feingold et al. | 606/107 |
| 6,168,621 | B1 | 1/2001 | Vrba | 623/1.2 |
| 6,203,558 | B1 | 3/2001 | Dusbabek et al. | 606/198 |
| 6,315,790 | B1 | 11/2001 | Gerberding et al. | 623/1.11 |
| 6,332,874 | B1 | 12/2001 | Eliasen et al. | 604/174 |
| 6,348,065 | B1 | 2/2002 | Brown et al. | 623/1.16 |
| 6,350,277 | B1 | 2/2002 | Kocur | 623/1.11 |
| 6,374,476 | B1 | 4/2002 | Ponzi et al. | 29/527.1 |
| 6,395,008 | B1 * | 5/2002 | Ellis et al. | 606/108 |
| 6,398,709 | B1 * | 6/2002 | Ehr et al. | 600/3 |
| 6,447,522 | B2 * | 9/2002 | Gambale et al. | 606/108 |
| 6,447,540 | B1 | 9/2002 | Fontaine et al. | 623/1.12 |
| 6,458,138 | B1 | 10/2002 | Sydney et al. | 606/108 |
| 6,500,285 | B2 | 12/2002 | Pepin et al. | 156/86 |
| 6,508,806 | B1 | 1/2003 | Hoste | |
| 6,530,947 | B1 | 3/2003 | Euteneuer et al. | 623/1.11 |
| 6,544,218 | B1 | 4/2003 | Choi | |
| 6,575,959 | B1 | 6/2003 | Sarge et al. | 604/533 |
| 6,746,424 | B2 | 6/2004 | Stamberg | 604/103.06 |
| 2001/0051784 | A1 * | 12/2001 | Brisken et al. | 604/22 |
| 2002/0038103 | A1 | 3/2002 | Estrada et al. | 604/103.09 |
| 2002/0049424 | A1 | 4/2002 | Fulford | 604/529 |
| 2002/0055770 | A1 | 5/2002 | Doran et al. | 623/1.15 |
| 2003/0055449 | A1 | 3/2003 | Lee et al. | 606/194 |
| 2003/0069522 | A1 * | 4/2003 | Jacobsen et al. | 600/585 |

FOREIGN PATENT DOCUMENTS

| | | |
|---|---|---|
| EP | 0884060 | 5/1998 |
| WO | 9944666 | 9/1999 |
| WO | WO 99/48548 | 9/1999 |
| WO | 0189620 | 11/2001 |

* cited by examiner

CATHETER TIP

BACKGROUND OF THE INVENTION

This invention relates generally to catheters, and more specifically to an assembly and method that may be used for delivering and deploying one or more implantable medical devices, such as a stents, grafts, stent-grafts, vena cava filters, or other implantable medical devices, hereinafter referred to collectively as stents, within a body lumen.

Guide catheters and diagnostic catheters are well known for use in the performance of medical procedures, such as coronary catheterization, angiography, angioplasty, and other diagnostic or interventional procedures, such as interventional radiology. Guide catheters aid in treatment of arterial lesions by providing a conduit for positioning dilatation balloon systems across an arterial stenosis. Guide catheters and diagnostic catheters work with various assemblies for performing other medical, therapeutic, and diagnostic procedures, such as dye delivery, arterial flushing, or arterial pressure monitoring.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Self-expanding, inflation expandable and hybrid stents are well known and widely available in a variety of designs and configurations. Examples are disclosed in U.S. Pat. No. 6,348,065, US 2002-0055770-A1 and U.S. Pat. No. 6,168,621, incorporated herein by reference. Inflation expandable stents are crimped to a reduced diameter configuration about the delivery catheter, then maneuvered to the deployment site and expanded to the vessel diameter by fluid inflation of a balloon positioned underneath the stent on the delivery catheter.

In advancing an inflation expandable stent through a body vessel to the deployment site, there are a number of important considerations. The stent must be able to securely maintain its axial position on the delivery catheter. The stent and inflation balloon in the reduced state must have a sufficiently small outer diameter to allow the catheter to be advanced through a tortuous anatomy into a desired location of a body lumen, such as an artery or other vessel. Further, advancement of the stent through the vessel is enhanced by increased flexibility of the stent and catheter tip at the catheter distal end. Radiopaque markers on the stent and/or catheter aid in precisely positioning the stent at the deployment site.

Delivery catheters, such as disclosed in U.S. Pat. No. 6,007,543 and incorporated herein by reference, are known in the art. Such catheters may include radiopaque markers and stent securement rings as disclosed in U.S. Pat. Nos. 6,530,947, 6,315,790 and 6,395,008, also incorporated by reference.

Current methods of assembling balloon catheters typically include several steps. Often times the catheter shaft is constructed by extruding one or more portions of the catheter shaft which are then assembled together with other components such as radiopaque markers, securement rings, etc. An inflation balloon is then positioned over and/or adjacent to the markers and securement rings and bonded to the shaft. In some cases, the distal tip or end region of the catheter may be provided with a tapered or other configuration. These steps typically require a skilled operator to properly assemble the various components of the catheter. Further, radiopaque markers, securement rings and even the balloon itself increase the outer diameter of the assembly.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, the present invention comprises a stent delivery catheter including a catheter shaft and a catheter distal end region or tip coupled to the catheter shaft. The catheter tip may be molded, and may include at least one hub portion. In some embodiments a hub portion is a portion of the shaft that is raised, indented, or other wise constructed to enhance engagement of the stent to the catheter shaft prior to delivery. Hub portions engage an unexpanded stent and help to prevent translocation of the stent along the catheter tip. In one embodiment the hub portion is formed integrally with the catheter tip, such as for example in embodiments wherein the tip is molded. In an embodiment wherein the hub portion comprises an indentation or recess in the tip, the recess may act as a storage recess for portions of a deflated expansion balloon. In some embodiments the catheter tip distal end may also include a tapered or radiused tip.

The catheter tip can further include at least one marker, which may be insert molded during formation of the catheter tip, or may be formed through injection molding or extrusion molding. Markers are desirably radiopaque markers that are viewable under fluoroscopy or MRI markers that are viewable through a magnetic resonance imaging system. Markers may comprise a piece of material that is separate from the catheter tip material, or may comprise a region of the catheter tip material entrained with another material to enable viewing under fluoroscopy or MRI. Markers may be positioned with the outer surface of the marker flush with the outer surface of the catheter tip. In some embodiments the marker may be fully embedded or recessed within the material of the tip. In some embodiments the marker may have a diameter that is raised relative to the surrounding tip. Such raised markers may also function as hub portions.

In at least one other embodiment, the catheter tip may include a stiffening insert, such as a spring. A stiffening insert may be insert molded during manufacture of the catheter tip.

In at least one other embodiment, at least a portion of the catheter tip material can include an entrained material that will alter flexibility of the tip. For example, carbon fibers may be included in the catheter tip material to reduce flexibility.

In at least one other embodiment, the delivery catheter comprises a catheter shaft coupled to a molded catheter tip, wherein said catheter tip has at least one recessed portion. The recessed portion may allow for greater flexibility of the catheter tip. Further, inclined portions of the recessed portion may engage an unexpanded stent and help to prevent translocation of the stent. The stent may further include raised hub portions that also help to prevent stent translocation.

These and other embodiments of the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described various embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
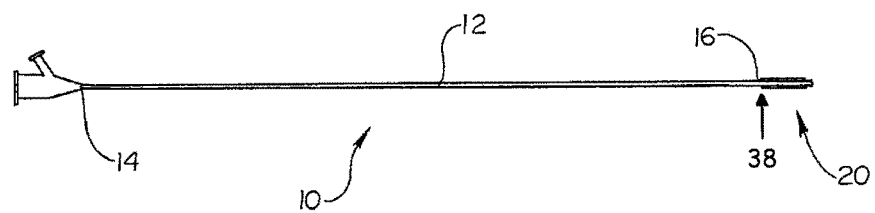
FIG. 1 depicts a catheter assembly in accordance with the present invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring generally to FIG. 1, an embodiment of a stent delivery catheter 10 is shown having a catheter shaft 12 and a catheter tip 20. The catheter shaft 12 has a proximal end 14 and a distal end 16, and further comprises a lumen 18 extending therethrough (see FIG. 2). The catheter tip 20 is coupled to the catheter shaft distal end 16 at a coupling 38.

The catheter shaft 12 and catheter tip may be made from any suitable material, such as polyesters and copolymers thereof such as those sold including polyalkylene terephthalates such as polyethylene terephthalate (PET) and polybutylene terephthalate (PBT) available under the tradename of EKTAR® available from Eastman Chemical Co. in Kingsport, Tenn., polycyclohexylene terephthalate (PCT); poly (trimethylene terephthalate) (PTT), PCTG and poly(cyclohexanedimethanol-co-ethylene terephthalate) (PETG) copolyesters available under the tradename of EASTAR® available from Eastman Chemical Co., PCTA available under the tradename of DURASTAR® available from Eastman Chemical Co., poly(ethylene naphthalate) (PEN) polyester available from DuPont in Wilmington, DE under the tradename of TEONEX®; and so forth; polyester elastomers (PEELs); polyamides such as amorphous nylon and nylon 12 such as those available from Elf Atochem under the tradename of CRISTAMID® and copolymers thereof such as GRILAMID® TR-55-LX nylon 12 polyether-block-amide available from EMS-American Grilon in Sumter, S.C.; polyetherimides available from GE Plastics under the tradename of ULTEM®; polystyrene and expandable polystyrene (EPS); acrylonitrile-butadiene-styrene (ABS); styrene-acrylonitrile (SANs); polyphenylene sulfide (PPS); polyphenylene oxides (PPO); interpolymers of PPO and EPS; polyetherketones (PEEK); polyolefins such as polyethylenes and polypropylenes including low, medium and high densities such as HDPE available under the tradename of ALATHON® from Equistar Chemicals; amorphous polyolefins; polyether-block-amides such as those sold under the tradename of PEBAX® available from Elf Atochem; polyimides; polyurethanes; polycarbonates; polyethers; silicones; as well as any copolymers thereof. The above list is intended for illustrative purposes only, and is not intended to limit the scope of the present invention. One of ordinary skill in the art has knowledge of such polymeric materials.

The catheter tip 20 may be made from any suitable material, such as described above, and is desirably more flexible than the catheter shaft 12. The catheter tip 20 is desirably made from a soft material, such as Pebax 40D, Pebax 55D or silicone.

The catheter tip 20 may be attached to the catheter shaft 12 using any suitable process, such as gluing, heat bonding, RF welding or laser welding. When using heat bonding techniques, the catheter shaft 12 and catheter tip 20 are desirably made from materials having similar melting temperatures.

Various embodiments of inventive catheter tips 20 are depicted in FIGS. 2-13. Catheter tips 20 desirably comprise an elongate tubular body having a proximal end 22, a distal end 24, a lumen 26 extending therethrough, a distal shaft portion 42 and a main shaft portion. The main shaft portion may be defined as the portion of the catheter tip 20 not defined as the distal shaft portion 42. The main shaft portion can have a greater length then the distal shaft portion 42. The catheter tips 20 may optionally include one or more hub portions 30, one or more markers or marker portions 32, one or more recessed portions 34, one or more stiffeners or reinforcements 28 and a radiused tip 36.

A balloon 44 generally includes a proximal waist portion 54 and a distal waist portion 56. A balloon 44 can be coupled at its proximal waist portion 54 to an outer catheter shaft 40, and at its distal waist portion 56 to the catheter tip 20 distal shaft portion 42. The length of the balloon 44 may be substantially coextensive with the catheter tip 20 main shaft portion. The catheter tip 20 may be coupled to the catheter shaft distal end 16 near the balloon proximal waist portion 54. In some embodiments, the coupling 38 may be proximal to the balloon proximal waist portion 54. In some embodiments, the coupling 38 may be distal to the balloon proximal waist portion 54.

In some embodiments, the catheter tip 20 may include a medical device mounting region, such as for mounting a stent, and the mounting region can be distal to the coupling between the catheter shaft 12 and catheter tip 20.

Desirably, catheter tips 20 are formed using a molding process or an extrusion process. Both a molding process and an extrusion process allow the catheter tip 20 to be precisely formed having sections of varying diameter. Thus, hub portions 30, recessed portions 34 and a radiused tip 36 may be integrally formed during tip manufacture, without separate installation or grinding steps.

Further, if the catheter tip 20 is formed with an injection molding process, portions of various embodiments, such as markers 32 or stiffeners 28, may be inserted into the mold prior to material injection. Thus, markers 32 and stiffeners 28 may be insert molded upon the catheter tip 20.

Figure 3:
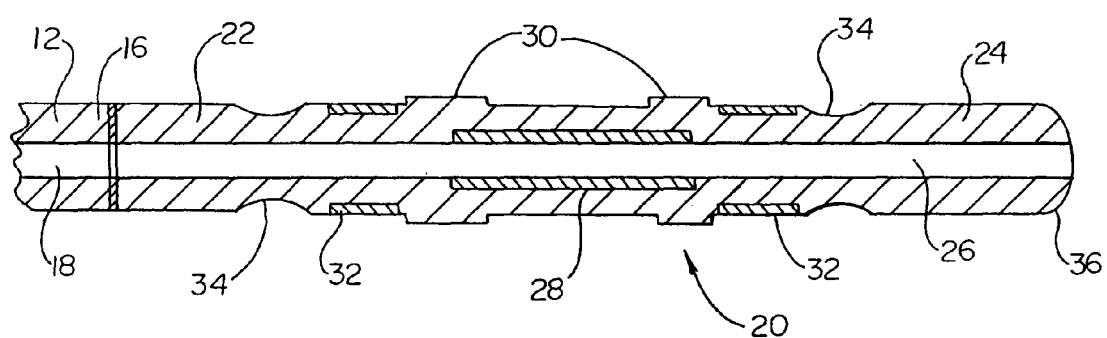
FIG. 3 shows a cross-sectional side view of an embodiment of an inventive catheter tip.

One or more stiffeners 28 may be used to increase rigidity of the catheter tip, as depicted in FIG. 3. A stiffener 28 is desirably insert molded into the catheter tip 20, and may comprise a strip of material, a cylinder of material, or the like. In one embodiment, the stiffener 28 may comprise a cylindrical coil of wire or a spring. A stiffener 28 may work to resist kinking of the catheter tip 20.

Figure 2:
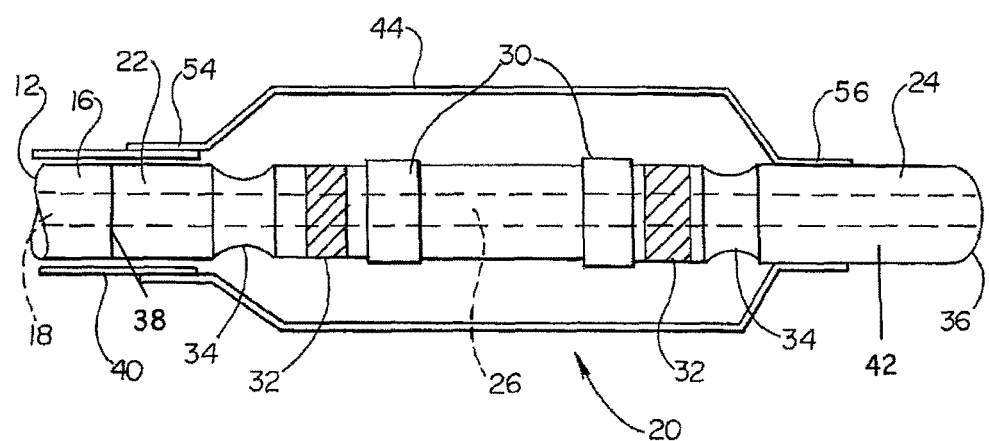
FIG. 2 depicts an embodiment of an inventive catheter tip.

Markers 32 may comprise radiopaque markers, MRI markers, and the like. Markers 32 may be of any suitable shape and desirably comprise circumferential bands, as depicted in FIGS. 2 and 3. In one embodiment, markers 32 may be inserted into the mold during manufacture of the catheter tip 20. As such, material used to form the catheter tip 20 forms around the marker 32 during the molding process, thereby securing the marker 32 in place without the use of adhesive or a separate installation step. Insert molding additionally allows the markers 32 to have a lower profile than is typically achieved with conventional assembly. Desirably, the outer surface of any markers 32 may be flush with the outer surface of the catheter tip 20, or even recessed beneath the surface.

In some embodiments, the markers 32 may be raised, or otherwise protrude above the outer surface of the catheter tip 20. The markers 32 may even function as hub portions 30.

In some embodiments, the catheter tip 20 may be used in a stent delivery system, and may be used to deliver inflation expandable, self-expanding or hybrid stents. Inflation expandable stents are generally crimped about the delivery catheter and the deflated balloon 44. After being maneuvered to the deployment site, the inflation expandable stent is expanded to the vessel diameter by fluid inflation of the balloon 44. A self-expanding stent is generally formed from a shape-memory material, such as Nitinol, and held in a reduced diameter about a catheter with a sheath. Upon removal of the sheath, a self-expanding stent will deploy to a deployment diameter. The delivery system for a self-expanding stent may or may not use a balloon 44.

Markers 32 are desirably located at a position corresponding to eventual placement of end portions of a stent that may eventually be installed about the catheter tip 20. Thus, the stent end portions may be adjacent to or otherwise aligned with the markers 32.

Radiopaque markers 32 may be any suitable material, including barium, bismuth, tungsten, gold, titanium, iridium, platinum, palladium, silver, rhenium, alloys of these materials, and others, such as disclosed in U.S. Pat. No. 6,315,790, incorporated herein by reference. MRI markers 32 may be any suitable material, and desirably a ferro-magnetic, superparamagnetic or paramagnetic material in such a quantity that the magnetic field surrounding the catheter tip 20 is disturbed enough to visualize the marker 32 on a magnetic resonance imaging system, such as gadolinium, iron or manganese containing alloys. Further, the markers 32 may be positioned with a portion raised above the surface of the catheter tip 20, and may also be used as a hub to prevent translocation of an unexpanded stent.

A molding process is also beneficial in that placement of various features of the catheter tip 20 is consistent for all tips 20 manufactured from a given mold. Hub portions 30, markers 32, stiffeners 28 and recessed portions 34 may be placed precisely and consistently in relation to the ends of the catheter tip 20, as well as in relation to each other.

Figure 4:
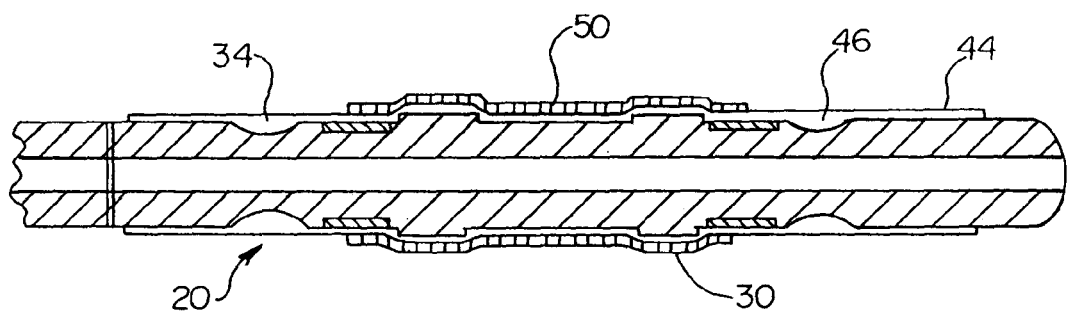
FIG. 4 shows a cross-sectional side view of an embodiment of an inventive catheter tip and a stent in an unexpanded configuration.
Figure 5:
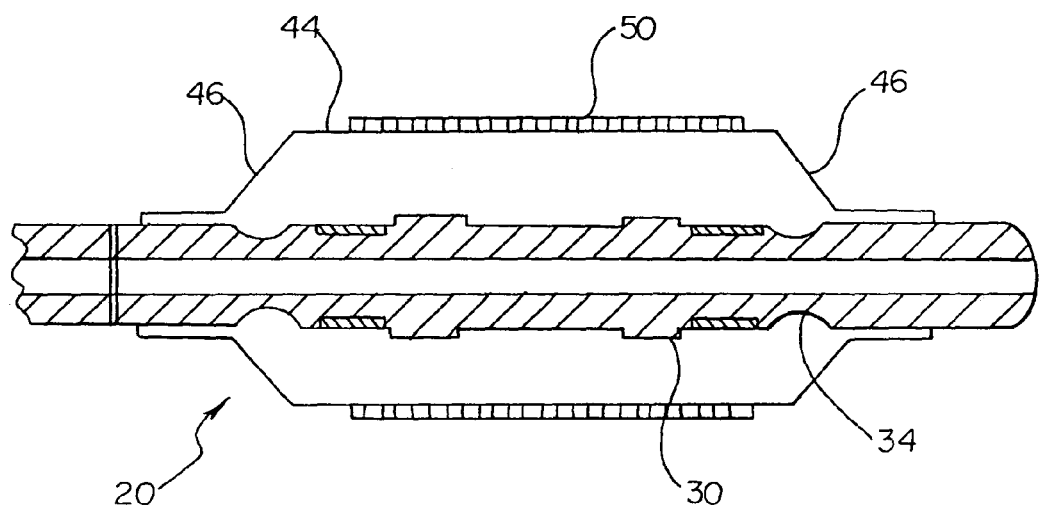
FIG. 5 shows a cross-sectional side view of an embodiment of an inventive catheter tip and a stent in an expanded configuration.

Referring to FIGS. 4 and 5, hub portions 30 may help to prevent a stent 50 from translocating proximally or distally when the stent 50 is in an unexpanded state, such as crimped to the catheter tip 20.

Recessed portions 34 may be located strategically to allow a catheter assembly to have a lower profile in desired locations. An expansion balloon 44 may include conical portions 46 where the diameter of the balloon 44 increases or decreases rapidly, as best shown in FIG. 5 with the balloon 44 in an expanded configuration. When the balloon 44 is installed on a conventional catheter in an uninflated configuration, the conical portions 46 may bunch undesirably to create a larger outer diameter. Recessed portions 34 in the catheter tip 20 may be located to act as a storage recess for portions of the balloon, for example the conical portions 46, thereby allowing the catheter tip assembly to have a lower profile in those sections.

Further, recessed portions 34 allow for greater flexibility of the catheter tip 20 in bending about the longitudinal axis. This aids in advancement of the catheter through a tortuous anatomy en route to a stent deployment site. However, if a greater flexibility is not desired in the regions of recessed portions 34, stiffeners 28 may be used appropriately for added rigidity.

Additional embodiments of catheter tips 20 may include various combinations of the features described herein. For example, an embodiment may include a single hub portion 30, and have no recessed portions 34 and no markers 32. Another embodiment may include a single marker 32 and a radiused tip 36.

Figure 6:
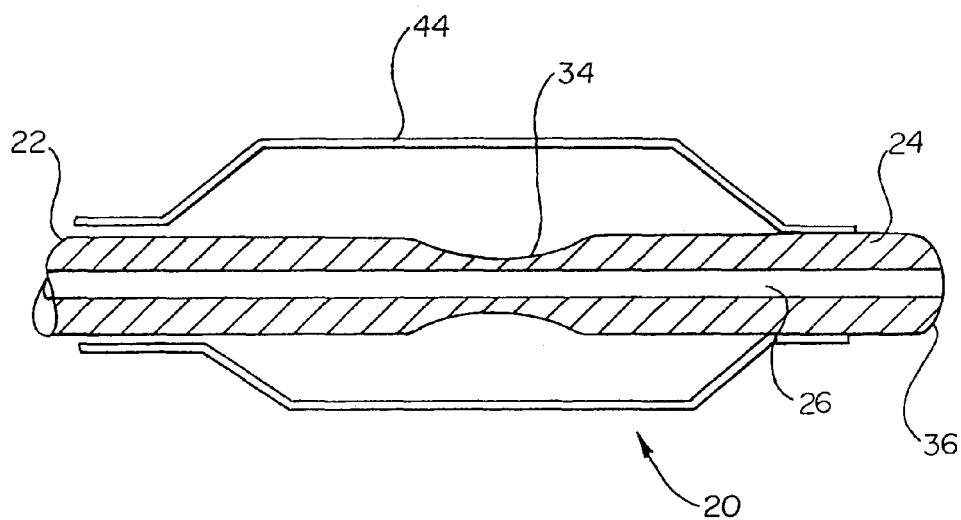
FIG. 6 depicts a cross-sectional side view of an embodiment of an inventive catheter tip.

Referring to FIG. 6, an embodiment of a catheter tip 20 is depicted having a large central recessed portion 34. In this embodiment, the large recessed portion 34 may act as a securement recess to help prevent translocation of an unexpanded stent. The recessed portion 34 also allows for greater flexibility of the catheter tip 20 in bending about the longitudinal axis.

Figure 7:
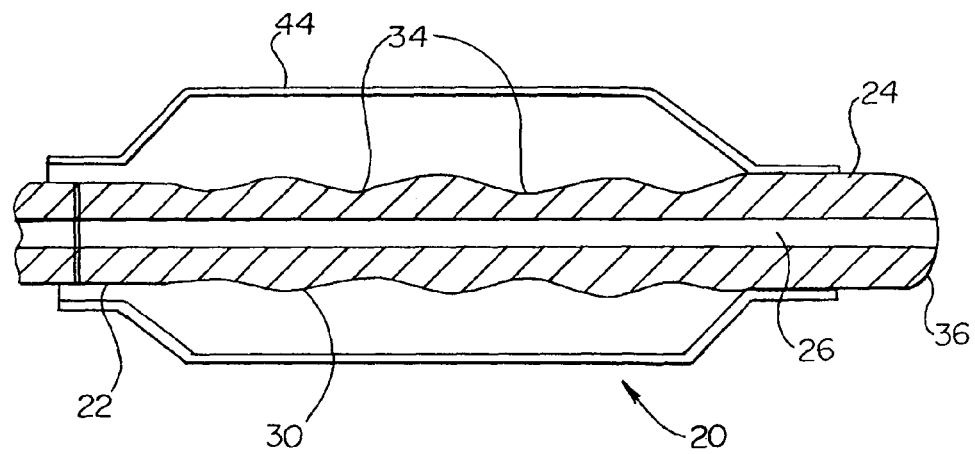
FIG. 7 depicts a cross-sectional side view of an embodiment of an inventive catheter tip.

A further embodiment, having multiple recessed portions 34 is depicted in FIG. 7. In this configuration, the catheter tip 20 has an undulating or serpentine surface along a portion of its length. Multiple recessed portions 34 can be more effective at securing an unexpanded stent than a single, larger recessed portion. Multiple recessed portions 34 also allow an increase in longitudinal flexibility across a greater length of the catheter tip 20. Adjacent recessed portions 34 may have varying outer diameters. Further, portions of the catheter tip 20 between adjacent recessed portions 34 may function as securement hubs 30, and may have a greater outer diameter than the tip proximal end 22 or the tip distal end 24.

Figure 8:
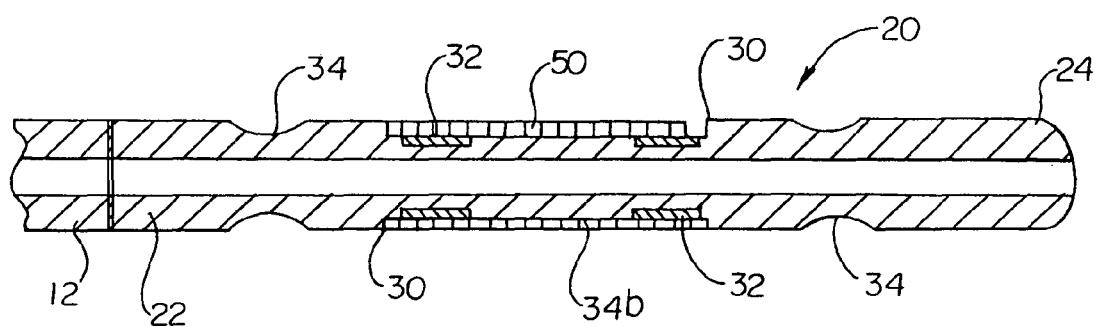
FIG. 8 depicts a cross-sectional side view of an embodiment of an inventive catheter tip.

FIG. 8 shows an embodiment wherein the catheter tip 20 includes a large recessed portion 34b. In this configuration, a stent 50 may be mounted upon the tip 20 such that the outer surface of the stent 50 may be flush with the tip 20 outer diameter, or even recessed beneath the tip 20 outer diameter. Markers 28 are further recessed within the large recessed portion 34b, and thus may be located proximal to ends of the stent 50. Further, portions of the catheter tip 20 that are directly adjacent to the ends of the stent 50 can act as securement hubs 30 and prevent the stent 50 from translocating.

Figure 9:
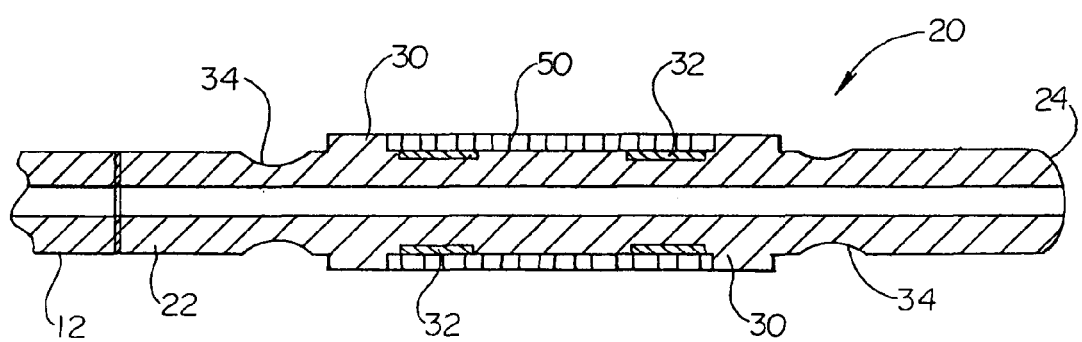
FIG. 9 depicts a cross-sectional side view of an embodiment of an inventive catheter tip.

FIG. 9 depicts another embodiment of a catheter tip 20, wherein securement hubs 30 are located outwardly from the markers 28. In this embodiment, a stent 50 may be mounted upon the tip 20 such that the outer surface of the stent 50 may be flush with the securement hubs 30, or nested between the securement hubs 30. Markers 28 may be located proximal to the ends of the stent 50.

In another embodiment, the catheter tip 20 may be formed having various regions, each region having properties that may be different from the other regions of the tip 20. For example, a region may comprise a marker region, and thus have radiopaque or magnetic properties. A region may also be more or less flexible than an adjacent region. Various regions may have differing melting points, and a catheter tip 20 may be molded utilizing a multiple step process wherein a first material composition is injected into a first mold to form a portion of the tip, which can then be inserted into a second mold, and a second material composition may be injected. Properties of regions may be adjusted via the use of various materials in forming the regions of the catheter tip 20. Thus, a catheter tip 20 manufactured to have marker regions may have radiopaque material entrained with the polymer material for that region, and would not require a separate radiopaque marker 32 in order to be viewable under fluoroscopy.

Figure 10:
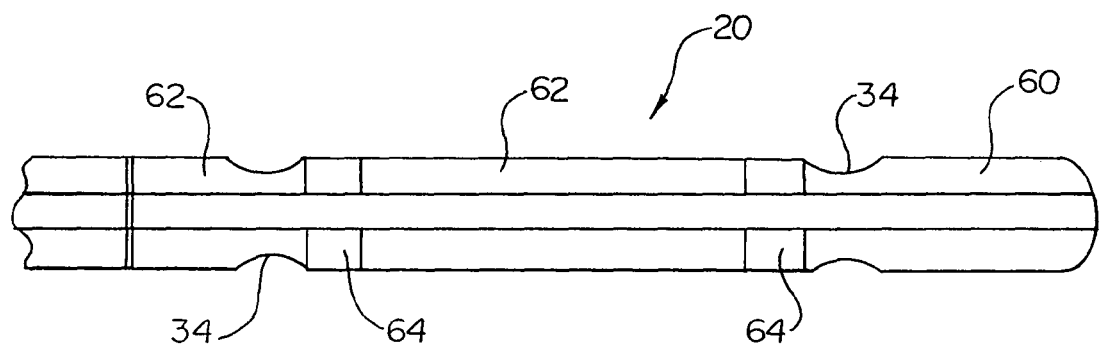
FIG. 10 depicts a cross-sectional side view of an embodiment of an inventive catheter tip.

FIG. 10 shows a catheter tip 20 comprising a first region 60, one or more second regions 62, and one or more marker regions 64. The first region 60 may comprise a soft distal region. A first region 60 may be made from a first matrix material composition. A second region 62 may have reduced flexibility as compared to a first region 60. A second region may be made from a second matrix material composition. A first matrix material composition may include portions of materials that are also present in a second matrix material composition. A reduced flexibility may be accomplished, for example, by including stiffening fibers within the polymer used to form the second region 62. Stiffening fibers can include carbon fibers, polypropylene fibers, polyolefin fibers, or any other material to accomplish an appropriate reduction in flexibility.

A marker region 64 can be visible under fluoroscopy or MRI. A radiopaque region may be formed by including radiopaque material in the region. For example, up to 90% bismuthoxide by weight may be loaded into the polymer matrix. Other materials include ceramic materials such as tungsten carbide, tungsten boride, and the like, and metals such as platinum, tantalum, iridium, tungsten, rhenium gold and alloys of such metals. An MRI region may be similarly formed using any appropriate material, such as terbiumoxide, gadoliniumoxide and dysrosiumoxide.

Regions of the catheter tip 20 may be formed using any suitable methods, such as molding or extrusion. For example, each region may be injection molded, and each region may be formed with an individual injector. Methods of forming an extrusion having alternating materials are disclosed in U.S. Pat. No. 5,622,665, incorporated herein by reference.

Catheter tips 20 having regions of varying stiffness and marker regions may also include all of the features of inventive catheter tips 20 described herein, such as recessed portions 34, securement hubs 30, markers 32 and stiffeners 28. In some embodiments, marker regions 64 may include a raised portion and function as a securement hub 30. In some embodiments, the entire stent mounting region may comprise a marker region 64. Further, a region may comprise both a marker region 64 and a region of reduced flexibility.

Figure 11:
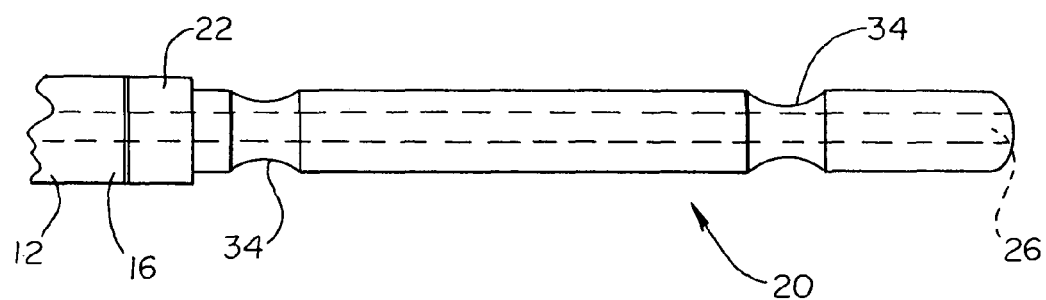
FIG. 11 depicts a side view of an embodiment of an inventive catheter tip.
Figure 12:
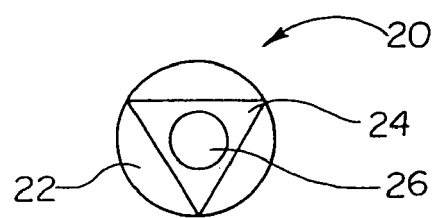
FIG. 12 depicts a front view of an embodiment of an inventive catheter tip.

In another embodiment, portions of the catheter tip 20 may have various cross-sectional shapes. FIGS. 11 and 12 depict a catheter tip 20 having a triangular cross-sectional portion. In some embodiments, a varying cross-sectional shape portion can be formed wherein the cross-sectional shape has a reduced cross-sectional area when compared to the catheter shaft 12. Areas where a cross-sectional shape does not extend to the catheter shaft 12 diameter may be described as reduced profile zones. In other embodiments, cross-sectional area of a shaped portion may be greater than that of the catheter shaft 12.

A shaped cross-sectional portion may be better suited to receive an unexpanded balloon than a circular cross section. In some embodiments, the folds of an unexpanded balloon may be located in a reduced profile zone, and as such, the balloon may have a lower cross-sectional profile than that of the catheter shaft 12.

A shaped cross-sectional portion may be of any shape desired. Various embodiments include a square, pentagon, hexagon, and the like. The number of sides of the shape may increase until the shape becomes substantially circular.

A catheter tip 20 having a shaped cross-sectional portion may also have circular portions which are of the same dimensions as the catheter shaft 12. As depicted in FIG. 11, the catheter tip 20 proximal end 22 is of the same shape as the catheter shaft 12.

Catheter tips 20 that include a shaped cross-sectional portion may also include all of the features of inventive catheter tips 20 described herein, such as regions of varying stiffness and marker regions, recessed portions 34, securement hubs 30, markers 32 and stiffeners 28.

Figure 13:
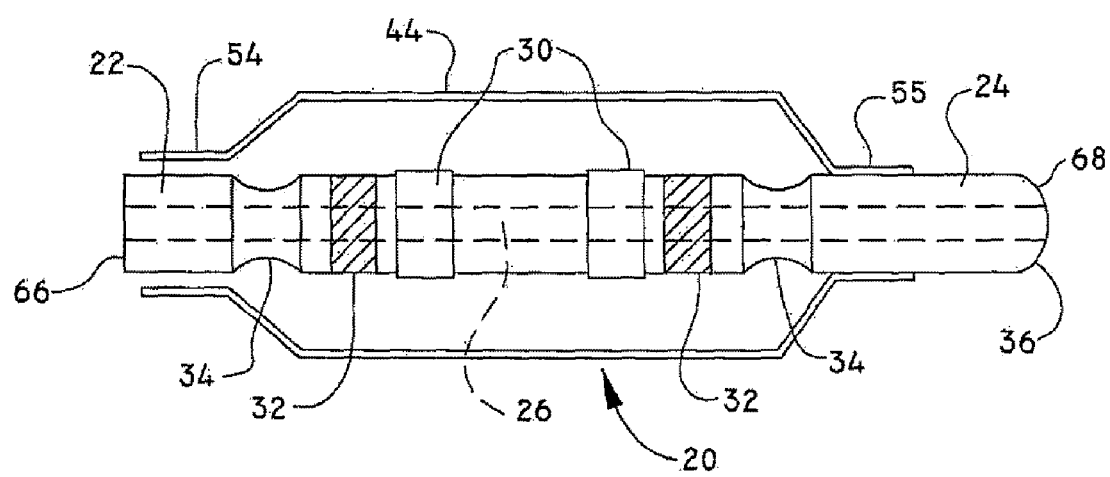
FIG. 13 depicts a side view of an embodiment of an inventive catheter tip.

In another embodiment, a catheter tip 20 may be separate from a catheter shaft 12. A separate catheter tip 20 can later be coupled to a catheter shaft 12. FIG. 13 shows a separate catheter tip 20. A catheter tip 20 may have a first free end 66 and a second free end 68. The catheter tip 20 may have a longitudinal axis, a length along the longitudinal axis, a width orthogonal to the length, and a height orthogonal to both the length and the width. The catheter tip 20 length can encompass a range to be suitable for delivery of a range of medical devices. For example, the catheter tip 20 may have a length of 4 millimeters in some embodiments, and a length of 70 millimeters in some other embodiments. The length of the catheter tip 20 can also vary in relation to the width or diameter. The length can be 4 times the width or diameter in some embodiments, and 70 times the width or diameter in some other embodiments. Many other specific lengths may be utilized according to the particular application. The catheter tip 20 can include a balloon 44. The main shaft portion of the catheter tip 20 can be substantially coextensive with the balloon 44.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of various embodiments of the invention. Those skilled in the art may recognize other equivalents to the specific embodiment described herein which equivalents are intended to be encompassed by the claims attached hereto.

The invention claimed is:

1. A catheter comprising:
a catheter shaft having a proximal end and a distal end;
an inflation balloon having a proximal waist portion, a proximal cone portion, a main body portion, a distal cone portion and a distal waist portion; and
a catheter tip having a guidewire lumen extending therethrough, the catheter tip comprising a proximal end, a distal end, a proximal shaft portion, a central shaft portion and a distal shaft portion, a cross-sectional area of the central shaft portion defined by a single peripheral layer of catheter tip material extending around said guidewire lumen, said cross-sectional area of the central shaft portion being substantially equal to a cross-sectional area of the proximal shaft portion and substantially equal to a cross-sectional area of the distal shaft portion, said catheter tip comprising a first balloon storage recess located between the distal shaft portion and the central shaft portion and a second balloon storage recess located between the central shaft portion and the proximal shaft portion, each balloon storage recess extending around a full outer periphery of the catheter tip, said balloon storage recesses not in fluid communication with said guidewire lumen, a cross-sectional area of the catheter tip at the first balloon storage recess being less than said cross-sectional area of the central shaft portion, a cross-sectional area of the catheter tip at the second balloon storage recess being less than said cross-sectional area of the central shaft portion, said catheter tip and said catheter shaft defining discrete structures, said catheter tip proximal end being coupled to said catheter shaft distal end, said balloon distal waist portion being attached to said catheter tip distal shaft portion; the first balloon storage recess oriented beneath the balloon distal cone portion and the second balloon storage recess oriented beneath the proximal cone portion, in an unexpanded state at least a portion of the balloon being stored in the first balloon storage recess.

2. The catheter of claim 1, further comprising at least one marker oriented beneath the balloon main body portion.

3. The catheter of claim 2, wherein said marker is a radiopaque marker.

4. The catheter of claim 1, wherein the catheter tip proximal end is coupled to said catheter shaft distal end at a coupling located proximal to said inflation balloon.

5. The catheter of claim 1, wherein said catheter tip distal end comprises a radiused tip.

6. The catheter of claim 1, wherein the balloon is unexpanded, at least a portion of the balloon distal cone portion is stored in the first balloon storage recess, and at least a portion of the balloon proximal cone portion is stored in the second balloon storage recess.

7. The catheter of claim 1, wherein said central shaft portion of the catheter tip further comprises a hub portion oriented beneath the balloon main body portion, the hub portion having a larger cross-sectional area than the central shaft portion.

8. The catheter of claim 7, wherein said catheter tip comprises a molded catheter tip and said hub portion is formed integrally with the catheter tip.

9. The catheter of claim 8, further comprising at least one marker.

10. The catheter of claim 9, wherein said radiopaque marker is insert molded.

11. The catheter of claim 9, wherein an outer surface of said radiopaque marker is flush with an outer surface of said catheter tip.

12. The catheter of claim 1, further comprising a stiffener.

13. The catheter of claim 12, wherein the stiffener is a spring.

14. The catheter of claim 1, wherein said catheter tip further comprises a marker region entrained with a radiopaque material.

15. The catheter of claim 1, wherein said catheter tip further comprises a first region and a second region, said first region having greater flexibility than said second region.

16. The catheter of claim 15, wherein said second region comprises entrained stiffening fibers selected from a group consisting of carbon fibers, polypropylene fibers and polyolefin fibers.

17. The catheter of claim 1, further comprising:
an outer catheter shaft;
wherein said balloon proximal waist portion is coupled to said outer catheter shaft.

18. The catheter of claim 1, wherein said catheter tip is coupled to said catheter shaft by heat bonding.

19. The catheter of claim 1, wherein said catheter tip is coupled to said catheter shaft by radio-frequency welding.

20. The catheter of claim 1, wherein said catheter tip is coupled to said catheter shaft with an adhesive.

21. The catheter of claim 1, wherein the catheter is a stent delivery catheter.

22. The catheter of claim 21, further comprising a stent mounted about the balloon.

23. The catheter of claim 22, wherein the stent is an inflation expandable stent.

24. The catheter of claim 22, wherein the stent is a self-expanding stent.

25. The catheter of claim 1, wherein at least a portion of the central shaft portion has a plurality of sides.

26. The catheter of claim 25, wherein the central shaft portion is triangular.

27. The catheter of claim 1, wherein the balloon main body portion is cylindrical.

28. A catheter comprising:
a catheter shaft having a proximal end and a distal end;
an inflation balloon having a proximal waist portion, a proximal cone portion, a distal cone portion and a distal waist portion; and
a catheter tip having a proximal end, a distal end, a main shaft portion and a distal shaft portion, the catheter tip comprising a recessed portion, a cross-sectional area of the recessed portion being less than a cross-sectional area of the catheter tip at a location proximal to the recessed portion and at a location distal to the recessed portion, the recessed portion oriented beneath the balloon distal cone portion, in an unexpanded state at least a portion of the balloon being secured in the recessed portion; said catheter tip comprising a first region and a second region, said first region having greater flexibility than said second region; said catheter tip and said catheter shaft defining discrete structures, said catheter tip proximal end being coupled to said catheter shaft distal end at a coupling located proximal to said inflation balloon, said balloon distal waist portion being attached to said catheter tip distal shaft portion; said catheter tip main shaft portion being substantially coextensive with said balloon;

wherein said second region comprises entrained stiffening fibers selected from a group consisting of polypropylene fibers and polyolefin fibers.

29. The catheter of claim 28, said catheter tip comprising a second recessed portion, a cross-sectional area of the second recessed portion being less than a cross-sectional area of the catheter tip at a location proximal to the second recessed portion and at a location distal to the second recessed portion;

wherein the balloon is unexpanded, at least a portion of the balloon distal cone portion is stored in said recessed portion, and at least a portion of the balloon proximal cone portion is stored in said second recessed portion.

* * * * *